(12) United States Patent
Hyland et al.

(10) Patent No.: US 8,239,138 B2
(45) Date of Patent: Aug. 7, 2012

(54) SCALING FACTOR FOR AN OUTPUT OF AN ELECTROCHEMICAL CELL

(75) Inventors: Mark Hyland, Yarnton (GB); Lindy Murphy, Yarnton (GB); Kevin Lorimer, Yarnton (GB)

(73) Assignee: Oxford Biosensors Ltd., Yarnton (GB)

( * ) Notice: Subject to any disclaimer, the term of this patent is extended or adjusted under 35 U.S.C. 154(b) by 1063 days.

(21) Appl. No.: 12/066,068

(22) PCT Filed: Sep. 7, 2006

(86) PCT No.: PCT/GB2006/003316
§ 371 (c)(1),
(2), (4) Date: Jun. 3, 2008

(87) PCT Pub. No.: WO2007/028998
PCT Pub. Date: Mar. 15, 2007

(65) Prior Publication Data
US 2009/0093979 A1    Apr. 9, 2009

(30) Foreign Application Priority Data

Sep. 10, 2005    (GB) .................................. 0518527.7

(51) Int. Cl.
*G01N 27/49*    (2006.01)
(52) U.S. Cl. ........... 702/19; 702/65; 702/104; 204/193; 204/194; 204/400; 204/401; 204/403.01
(58) Field of Classification Search .................. 702/19, 702/65, 104; 600/345–350, 365, 366; 205/775; 204/193, 194, 400, 401, 403.01
See application file for complete search history.

(56) References Cited

U.S. PATENT DOCUMENTS

| | | | |
|---|---|---|---|
| 2004/0194302 A1* | 10/2004 | Bhullar et al. | ............... 29/847 |
| 2005/0023137 A1 | 2/2005 | Bhullar et al. | |
| 2005/0163657 A1 | 7/2005 | Childers et al. | |

FOREIGN PATENT DOCUMENTS

| | | |
|---|---|---|
| DE | 4329742 A1 | 3/1995 |
| JP | 2000-019147 | 1/2000 |
| WO | 03029804 A1 | 4/2003 |
| WO | 03056319 A2 | 7/2003 |

OTHER PUBLICATIONS

PCT International Search Report for PCT/GB2006/003316, mailed Apr. 12, 2007.
Great Britain Search Report for Application No. GB0518527.7, dated Jan. 27, 2006.

* cited by examiner

*Primary Examiner* — Sujoy Kundu
(74) *Attorney, Agent, or Firm* — John K. Fitzgerald; Fulwider Patton LLP (57) ABSTRACT

A scaling factor for scaling an output of a first electrochemical cell, is determined in order to compensate for the effect on the output caused by an variation in value of a property of a working electrode of the first cell from a reference value of that property. A measured value for the property is obtained from a portion of material formed so as to have substantially the same value of the property as does the working electrode and the measured value is processed to generate the scaling factor.

13 Claims, 8 Drawing Sheets

SCALING FACTOR FOR AN OUTPUT OF AN ELECTROCHEMICAL CELL

RELATED APPLICATIONS

This is a U.S. national phase application of PCT/GB2006/003316, filed Sep. 7, 2006, which claims priority to United Kingdom Application No. 0518527.7, filed Sep. 10, 2005.

BACKGROUND

The present invention relates to a method of determining a scaling factor for scaling an output of an electrochemical cell. The scaling factor is for use in compensating for the effect on the output caused by any variation in a value of a property of a working electrode of the first cell from a reference value of that property.

In one embodiment the property is the thickness of the working electrode.

It will be understood that in the context of this patent "thickness" refers to the critical dimension of the working electrode. In one embodiment this is the width of a microband.

Sensors comprising electrochemical cells having micro-electrodes are used to detect or measure the concentration of a particular compound in a test sample. A biosensor comprising such a cell may for example be used to screen blood, urine or other such biological fluids for determination of their contents.

A cell having a micro-electrode and which may be used in a biosensor is described in our co-pending application WO 03/056319. The cell described in WO/03/056319, comprises a working electrode and a pseudo-reference electrode, at least one of which, typically the working electrode is a micro-electrode. A micro-electrode has at least one dimension not exceeding 50 micro meters. The working electrode is in the form of a band around the walls of the cell. An insulating material separates the working and counter electrodes. An electro-active substance is located in the cell and on contact of a measurement sample with the electro-active substance an electrochemical reaction may occur which may induce a measurable current, voltage or charge in the cell.

The electrochemical response of a microelectrode is a function of the electrode dimensions. For an electrochemical cell using a micro-band working electrode the thickness or width of the electrode constitutes the smallest dimension of the microelectrode dimensions. The measurable current also depends upon the thickness of the working electrode, so it is important to normalise for the variations in the thickness of the working electrode in order to accurately correlate the measured current to the concentration of the analyte.

In a biosensor the measurable current generated by an electrochemical reaction varies in a known relation to the concentration of the analyte under test. This known relation depends upon the thickness of the working electrode.

Currently, one approach for ensuring tight thickness tolerances for the working electrodes is to deposit the working electrodes using high vacuum techniques. Such techniques provide a uniform film deposition and are accurate. They are however economically expensive.

Other cheaper techniques for depositing working electrodes, for example, screen printing, ink jet printing, laminating, doctor blading and low vacuum deposition are less precise and provide working electrodes of unknown thickness and which vary in thickness across the sheet on which they are formed.

Embodiments of the present invention aims to alleviate the above-mentioned problems.

SUMMARY OF THE INVENTION

According to a first aspect, the present invention there is provided a method for determining a scaling factor for scaling an output of a first electrochemical cell, to compensate for the effect on the output caused by any variation in a value of a property of a working electrode of the first cell from a reference value of that property, the method comprising: obtaining a first measured value from a portion of material formed so as to have substantially the same value of the property as does the working electrode; and processing the first measured value to generate the scaling factor.

In certain embodiments the property is a physical dimension of the electrode portion, such as thickness or width. In the specification reference to determination of electrode thickness can generally be taken to be also the determination of electrode width as the terms are used synonymously herein.

In certain embodiments the portion of the material from which the measurement is obtained may be a portion of the working electrode itself.

According to a further aspect, the invention provides an arrangement comprising:
 a sensor comprising at least one electrochemical cell, a working electrode and a counter electrode; and
 a data tag for the sensor, the data tag carrying data representative of a correction/scaling factor to be applied by a meter when measuring the output of the sensor.

According to a further aspect, the invention provides a method of manufacturing an electrochemical sensor, the method comprising:
 forming a sensor having at least one electrochemical cell and a working electrode;
 conducting a measurement on the sensor relating to a parameter of the working electrode;
 tagging the sensor with a data tag which includes data representative of a correction or scaling factor to be applied to compensate for deviation of the measured parameter from a reference value for the parameter.

According to a further aspect, the invention provides a test sensor system comprising;
 a sensor comprising at least one electrochemical cell, a working electrode and a counter electrode and, a data tag for the sensor, the data tag including data representative of a correction or scaling factor to be applied when measuring the output of the sensor; and
 a meter for measuring the electrical output of the sensor and for retrieving the data from the data tag to apply the correction factor to the sensor output.

BRIEF DESCRIPTION OF THE DRAWINGS

Specific embodiments of the invention will now be described by way of example only with reference to the accompanying drawings in which:

FIG. 3A to 3E are schematic plan views of alternative track/electrode arrangements for different embodiments in accordance with the invention)

DETAILED DESCRIPTION OF THE PREFERRED EMBODIMENTS

Figure 1:
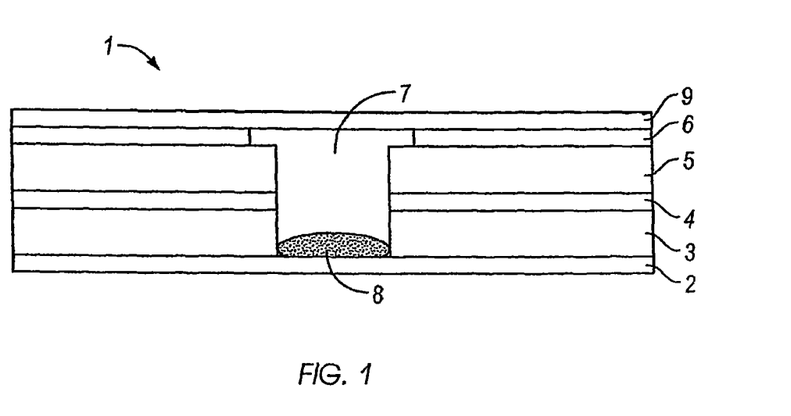
FIG. 1 is a schematic side view of an electrochemical cell.

Referring now to FIG. 1 of the accompanying drawings, an electrochemical cell 1, illustrated in a cross sectional side view, comprises a base layer 2 formed from a non-conducting porous material. The base layer 2 is preferably formed from PET or a laminated material and has a thickness of 100-250μm, preferably around 125μm.

A non-conducting supporting layer 3 is formed on the base layer 2. The supporting layer 3 is also preferably formed from PET and has a thickness in the range of 100μm to 500μm, preferably 250μm.

The supporting layer 3 forms a support on which a working electrode 4 is formed. The working electrode 4 is preferably in the form of a continuous band around the wall(s) of the cell 1. The thickness of the working electrode 4, which is its dimension in a vertical direction when the cell 1 is placed on the base 2, is typically from 0.01 to 50 micro meters. Preferred and other possible thicknesses of the working electrode are as described in our co-pending application WO 03/056319.

The working electrode 4 is preferably formed from carbon, for example in the form of conducting ink. A preferred carbon based conducting ink comprises a suspension of carbon dispersed in a resin solution. The working material may be formed of other materials and inks as detailed in WO 03/056319. Furthermore, two or more layers of the same or different materials may be used to form the working electrode.

A dielectric layer 5 comprising an insulating material typically a polymer, a plastic or ceramic again as detailed in WO 30 03/056319 is formed on and insulates the working electrode 4 from a pseudo-reference or counter electrode 6. Typically, the dielectric layer 5 is of thickness 1 to 1000μm. The dielectric layer could be formed of more than one layer.

The pseudo-reference or counter electrode 6 in a preferred 5 embodiment comprises silver/silver chloride and forms part of the top of the cell 1. Preferably the material of the counter electrode 6 is provided in the form of a conductive ink and the pseudo-reference electrode 6 has a thickness of the order of 5 microns or greater. A range of possible materials, inks and thicknesses suitable for the pseudo-reference electrode are also discussed in WO 03/056319.

In order to make the cell 1 the layers are deposited in a layer by layer fashion. In a preferred embodiment a working electrode 3 preferably formed of carbon is screen printed on the supporting layer 2 and the dielectric layer 5 is printed on the working electrode 3. The dielectric layer 5 may be printed as two layers so that any pin-holes that occur in the first layer of printing are filled. The pseudo-reference electrode 6, preferably formed of silver/silver chloride is screen printed on the dielectric layer 5. Laser drilling, mechanical punching or other drilling means is used to form a hole 7 through the dielectric layer 5, the working electrode 4 and the supporting layer 3. Preferably, the hole 7 has a diameter of about 0.5 to 25 1.0mm. Furthermore, the pseudo-reference electrode ends around 0.4 to 0.5mm from the edge of the hole 7.

The base layer 2 is fixed, for example by a suitable adhesive, to the un-printed side of the supporting layer 3 to produce the 30 base of the cell 1. The base layer 2 may take the form of a porous membrane containing air holes so that air in the well can be displaced when a measurement sample is introduced into the well formed by hole 7.

An electro-active substance 8 is contained within the hole 7. The electro-active substance 8 may be freeze dried to form a porous cake. On introduction of a measurement sample (not shown) into the well formed by hole 7 the electro-active substance 8 re-suspends and an electrochemical reaction may occur and a measurable current, voltage or charge may occur in the cell. Electro-active substances are discussed in more detail in our co-pending application WO 03/056319.

Preferably, the open end of the cell is covered with a membrane 9 that is permeable to components of the sample to be tested, for example blood. The membrane may also be used to filter out components of the sample that should not enter the cell, for example red blood cells.

Figure 2:
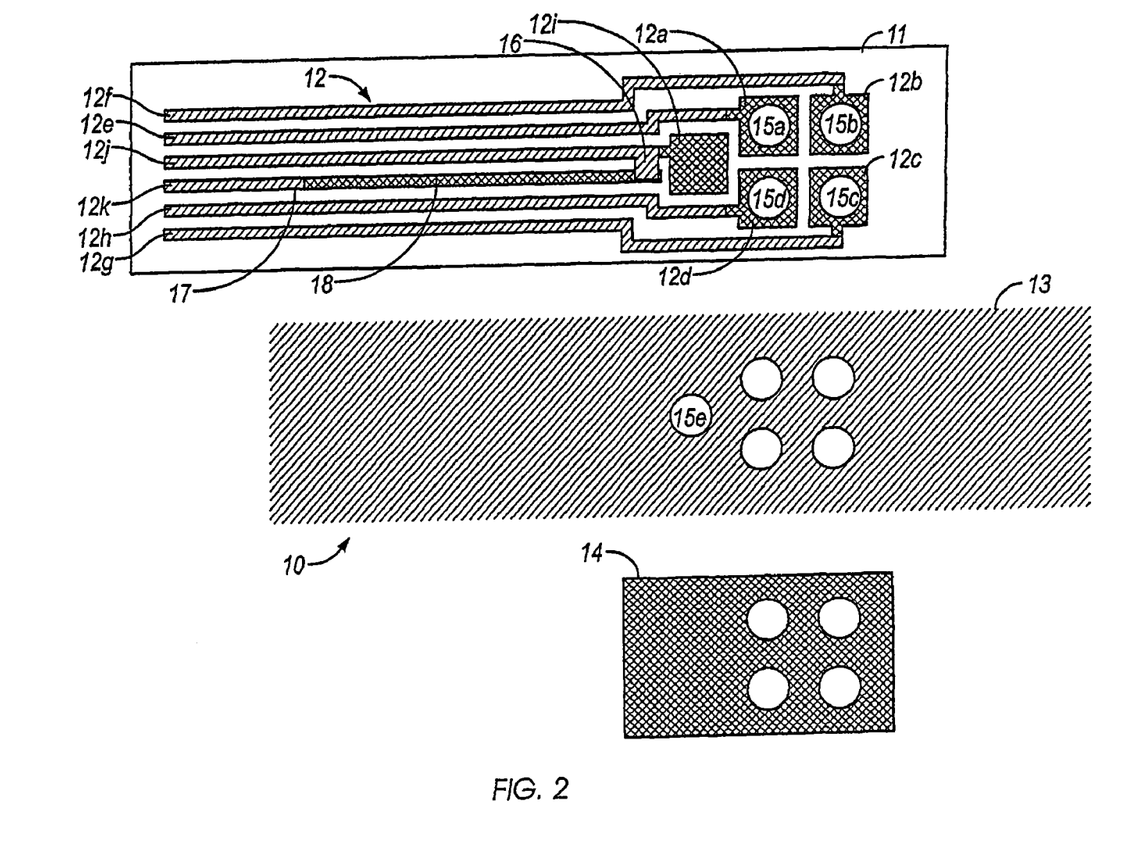
FIG. 2 is a schematic plan view of a sensor strip comprising four electrochemical cells.

Referring now to. FIG. 2 of the drawings, there is illustrated in a schematic plan view, layers of a sensor strip 10 comprising four electrochemical cells of the type and made as described above.

The sensor strip 10 comprises an insulating substrate sheet 11. Formed on the insulating substrate sheet 11 is a patterned layer 12 of material that forms four working electrodes 12a, 12b, 12c, and 12d, one for each of the respective four cells and four conductive tracks 12e, 12f, 12g, and 12h, each of which in electrical contact with a respective one of the four working electrodes 12a, 12b, 12c, and 12d.

The patterned layer 12 also defines an additional pad 12i, a fifth conductive track 12j, in electrical contact with the additional pad 12i, and an additional conductive track 12k.

In a preferred embodiment the patterned layer 12 is formed from carbon and is screen printed on the insulating substrate sheet 11.

The four cells each further comprises a dielectric insulating layer 13 deposited over the four working electrodes 12a, 12b, 12c, and 12d, and a pseudo-reference electrode layer 14, in a preferred embodiment formed from silver/silver chloride and screen printed on the dielectric layer 13.

It will be appreciated that for ease of viewing the various layers, the dielectric layer 13 and the pseudo-reference electrode layer 14 are each illustrated shifted laterally sideways from their true positions in the strip 10.

Each of the four cells further comprises a respective one of four holes 15a, 15b, 15c and 15d, formed through the, the dielectric layer 13 its respective working electrode 12a, 12b, 12c and 12d, and the supporting layer 11 ending at a base layer (not illustrated).

A fifth hole 15e, is printed on the dielectric layer 13 to the additional pad 12i. The pseudo-reference electrode 14 makes 25 electrical contact with the additional pad 12i.

Each of the four conductive tracks 12e, 12f, 12g, and 12h, allows the respective working electrode 12a, 12b, 12c, and 12d, with which it is in electrical contact to be placed in a circuit with the pseudo-reference electrode 14, measuring instruments and voltage sources.

Likewise, the fifth conductive track 12j, which is in electrical contact with the pseudo-reference electrode 14 via the additional pad 12i, allows the pseudo-reference electrode 14 to be placed in a circuit with any of the four working electrodes 12a, 12b, 12c, and 12d, measuring instruments and voltage sources.

If, the five conductive tracks 12e, 12f, 12g, 12h, and 12j, are formed from a relatively poor conductor like carbon, each also may comprise a second conductive layer (illustrated in grey in FIG. 2) formed from a more conductive material, for example, silver. This second conductive layer is preferably deposited before and hence underneath the first, although for reasons of clarity, it is illustrated as being above the first layer in FIG. 2.

It should be noted that this second conductive layer does not extend underneath any of the four working electrodes 12a, 12b, 2012c, and 12d, or underneath the additional pad 12i. In a preferred embodiment, where the first track layer is carbon and the second is silver an overall track resistance is reduced form around 2kΩ in the absence of the silver to around 200Ω in its presence.

In the example sensor strip 10 illustrated in FIG. 2 the additional conductive track 12k is electrically connected to the fifth conductive track 12j, and hence the pseudo-reference electrode 14 by a portion 16 of the second conductive layer. A first section 17 of the additional conductive track 12k comprises both the relatively poor conductor, for example carbon and underneath this, the better conductor, for example silver.

A second section 18 of the additional conductive track 12k comprises the relatively poor conductor only.

In an embodiment of the invention, additional conductive track 12k is used to obtain a measurement $I_{meas}$ of the current that flows through the track 12k when a predetermined voltage, for example 100, mv, is applied across the additional track 12k and the fifth conductive track 12j. The measurement $I_{meas}$ is indicative of the thickness of the in this example carbon, that forms the second section 18 of the track 12k. Thus this measurement is also indicative of the thickness of the carbon working electrodes 12a, 12b, 12C and 12d. These electrodes have the same thickness as the carbon in additional conductive track 12k, as they were deposited at the same time as the additional track 12j and under the same conditions.

As will be explained in more detail below, the measured value $I_{meas}$ may then be used in determining a normalising or correction factor F, which during a subsequent test on a sample using one or more of the cells can be used to compensate the current Output from a cell for the effect thereon of any variation in the working electrode thickness from a reference thickness.

Similarly $I_{meas}$ can be used to generate corrections factors for variations in other physical properties such as resistance of the carbon layer due to small variations in carbon ink composition or changes wrought by prolonged storage. Correction factors may also be generated for other properties, for example, surface roughness and charging current.

The correction factor F is a function of this variation in electrode thickness and preferably, P is obtained according to the equation:

$$F = 1 + K_1 N^X + K_2 N^Y$$

Where $N = (I_{nom} 13 I_{meas})/I_{nom}$ $K_1$ and $K_2$ are constants, which are specific to the electrochemical systems used on the strip and they may be calculated empirically. $K_1$ and $K_2$ may have different values for different electrochemical systems. $K_1$ and $K_2$ may take any value and it is possible for one or other to be zero.

X and Y are also constants specific to the electrochemical system or systems operating in the strip and may also be calculated empirically.

$I_{nom}$ is a notional average current value. In one embodiment, $I_{nom}$ is the average of current measurements obtained when the predetermined voltage is applied across the additional track 12k and the fifth conductive track 12e of each strip from a sample of strips, for example a thousand strips, produced in the same batch (or otherwise produced under the same conditions) as the strip 10. In this embodiment, $I_{nom}$ is indicative of the average thickness of the carbon working electrodes of the cells in the sample of strips.

In an alternative embodiment $I_{nom}$ is taken as an arbitrary value within limits determined by the sheet thickness. In essence, in this alternative embodiment, $I_{nom}$ is indicative of the thickness of a notional working electrode.

Thus for any given strip, $I_{meas}$ can be measured, the constants $K_1 K_2 X$ and Y are known and the relevant $I_{nom}$ can either be obtained from measurements from a sample of strips or selected as an arbitrary value. These values allow the correction factor F to be calculated for a given strip in accordance with the above equation.

In practice, F will be lower than the value 1 if the thickness of the additional track of the given strip is greater than the average thickness of the additional tracks of the strips in the sample (or greater than the thickness of the notional electrode), F will be higher than the value 1 if the thickness of the additional track of the given strip is less than the average (or less than the thickness of the notional electrode), and F will be equal to the value 1 if the thickness of the additional track of the given strip is equal to the average (or equal to the thickness of the notional electrode).

In this primarily described embodiment the thickness of the deposited additional track is effectively being measured by means of determining the electrical resistance of the track. The resulting measurement is used to obtain the correction factor F. As an alternative to a resistance measuring technique, other methods may be utilized in order to obtain a value representative of the thickness of the track and consequently arrive at a correction factor to be applied. For example techniques such as beta absorption, IR transmission, Tallysurf (or other piezoelectric techniques), ultrasound, thermal conductivity, rigidity or Youngs Modulus techniques could be utilized for determination of a correction or scaling factor. Additionally, it is to be understood that the invention encompasses techniques in which track variables other than thickness are compensated for such as for example density or porosity, by measuring the relevant property and deriving a correction or scaling factor dependant upon deviation of the measured value from a reference (normal) value.

The obtained correction factor F for a given strip is used to scale the electrochemical current generated by an electrochemical cell of the strip during analysis of an actual sample, for example, a blood sample. The meter or measurement apparatus used to measure the electrochemical current may be programmed with the correction factor F for that strip. After measuring the electrochemical current, the meter scales the current with the correction factor to generate a scaled current measurement. The scaled current reading is then used to calculate the concentration of one or more components in the sample.

Conveniently, each strip (or its packaging) may be provided with a data tag such as bar code encoding the correction factor for that strip and each measuring meter may be provided with a data tag reader, such as a bar code reader. Prior to tenting a sample, a user may program values for $I_{nom}$, K, X and Y into a meter by scanning the relevant bar code with the meter's bar code reader so that the necessary correction can be performed based on $I_{meas}$. The values may be programmed into the meter by other electronic or opto electronic data tag means, for example using RFID or using a ROM chip. Alternatively, data from the data tag may be input manually. The data tag may be applied to the sensor strip as a part of the manufacturing process, following a parameter measurement stage. The processing to obtain the scaling/correction factor may be effected prior to storing the data on the tag or subsequently (for example by the meter). The data tag may be representative of a single strip or may be representative of a batch of sensors, for example an array of sensors provided on a substrate sheet.

If the correction factor (or Imeas value) for the cells of a given strip is outside of an acceptable range, then this may indicate that the working electrodes for that strip are defective. If the meter detects that a correction factor (or Imeas value) is outside of this range then an error message may be presented to a user, prompting the user to use a fresh strip. The number of strips in a batch that are rejected in this way may be used to evaluate the stability of the ink used to make the strips.

Advantageously, embodiments of the invention allow the manufacture of sensor strips using the inexpensive techniques referred to in the introduction. Calculating an appropriate correction factor and applying it to a current produced when a sample is tested, compensates the current of the effect of any variation in the measuring parameters working electrode (e.g. thickness) norm value for the parameter for the batch average for the parameter or from the notional norm value for the parameter for the working electrode. Thus, for as example when track thickness is the parameter compensated for, meters configured to work with cells having working electrodes of thickness equal to that of the batch average thickness (or the thickness of the notional working electrode) can also work with cells whose working electrode thickness varies from this.

It will be appreciated that multiple strips 10 will be manufactured together on a single sheet. In one embodiment, each of the strips on a sheet is provided with its own additional conductive track 12. This need not be the case. In alternative embodiments, one or more additional tracks may be printed at specific locations on the sheet, each of which may be used to obtain measurements for one or more sensor strips.

The conductive tracks 12 and in particular the additional conductive track 12$k$ can have various configurations, and exemplary configurations are shown in FIGS. 3A to 3E. In the arrangement shown in FIG. 3A, the tracks are deposited in accordance with the embodiment of FIG. 2. The additional conductive track 12$k$ is connected to the conductive track 12; which is in electrical conduct with the pseudo reference electrode.

Figure 3A:
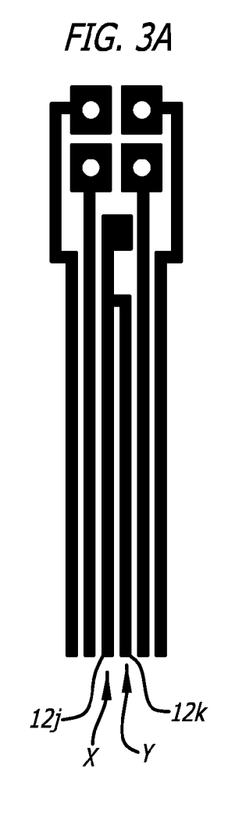
Figure 3B:
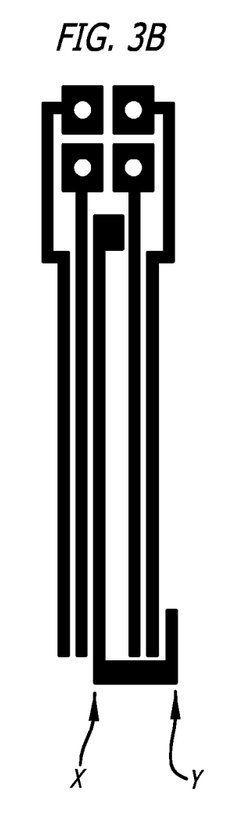

In the arrangement of FIG. 3B, the additional conductive track 12 forms an extension leg at the free end of the track 12; connected to the pseudo reference electrode. A short circuit current flow, when a voltage is applied across the track 12 between the points X and Y in the diagram.

Figure 3C:
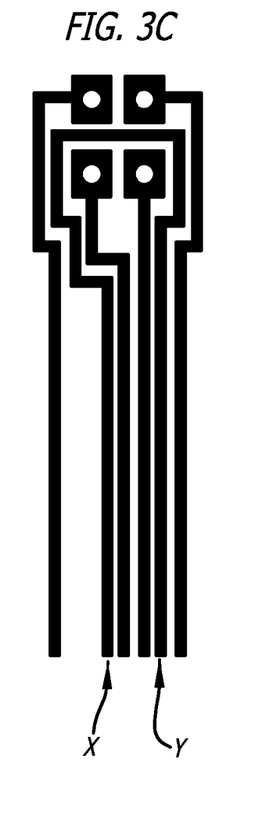
Figure 3D:
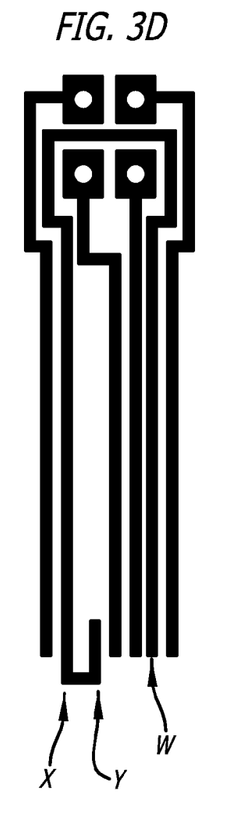

In the arrangement of FIG. 3C the additional conductive track 12$k$ extends from a free end X in a loop about the working electrodes 12a, 12d and returns to a second free end Y. A current flows in track 12$k$ when a voltage is applied across X and Y. The arrangement of FIG. 3D is generally similar to the arrangement of FIG. 3C however the track 12$k$ includes a terminal return portion at one of its free ends. A voltage can be applied across XY or XW to flow current either along a short length of track 12$k$ between X and Y or the longer length between X and W. Generally the results will be most representative of the relevant track parameter when using the longer length track length.

Figure 3E:
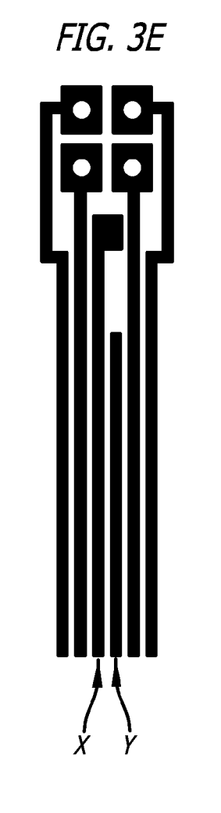

In the arrangement of FIG. 3E the track 12$k$ is entirely separate from the track 12$j$ connected to the pseudo reference (winter) electrode; The voltage can be applied across the ends X Y of track 12$k$ or at spaced positions along the length of track 12$k$.

In order to test operational characteristics, various exemplary trials have been conducted and the results obtained are presented in the following examples. Substrate sheets were printed with carbon electrode strip tracks (such as those shown in FIG. 3A). Each sheet had a 126electrode strips (7, rows, 18columns).

EXAMPLE 1

Variation of Sheet Resistance with Thickness of Carbon Layer

The electrode design was as shown in FIG. 3$a$. The resistance of each electrode was measured between the exposed carbon legs of the Counter Electrode 12; and extra leg 12$k$ with calibrated multimeter. An average was taken in order to get the average sheet resistance.

The thickness of the carbon layer was measured at centre of each sheet using a Mitutuyo surftest SV2000Tallysurf unit.

Figure 4:
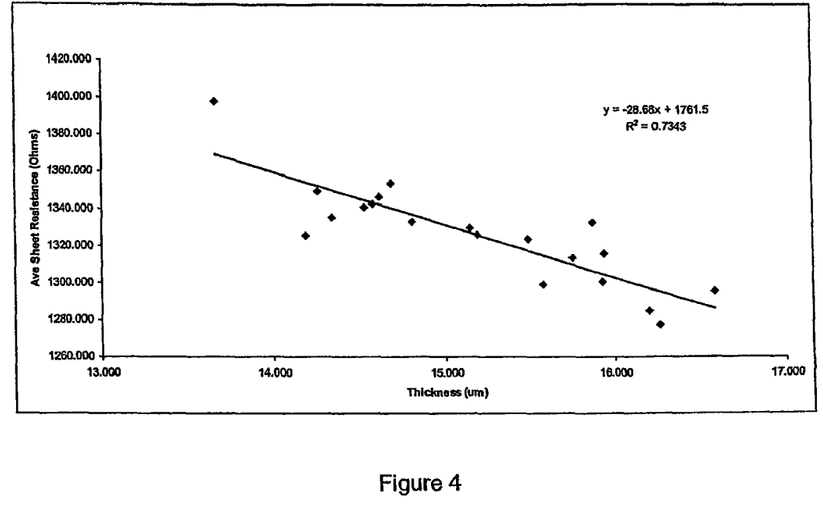
FIG. 4 is a graph showing variation of resistance with thickness for a carbon layer.

The average sheet resistance was plotted against the carbon thickness at the center of the sheet (FIG. 4). This shows that there is a correlation between the sheet resistance and the thickness of the carbon layer.

EXAMPLE 2

Figure 5:
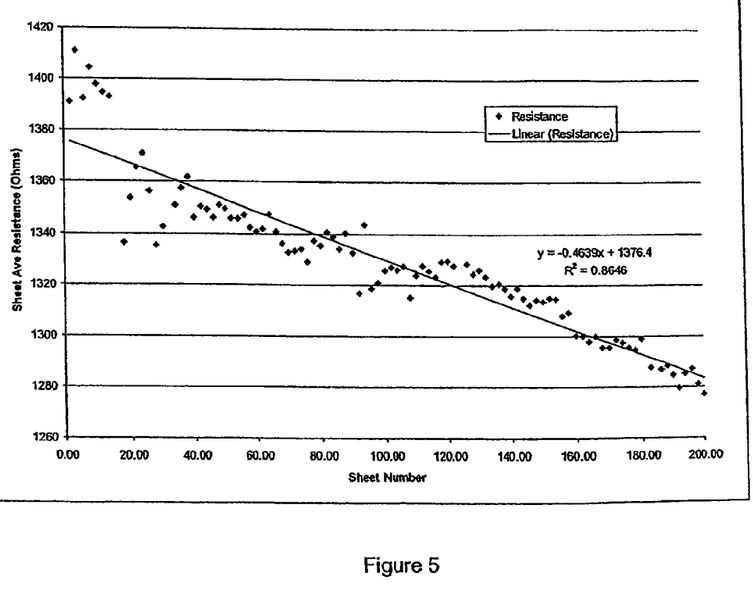
FIG. 5 is a plot showing average sheet resistance against sheet number.

The average sheet resistance was taken for every $2^{nd}$nd sheet in a batch. The resistance measured with calibrated multimeter between the exposed carbon legs of counter electrode (leg 12; and the extra leg 12$k$ for resistance measurement (FIG. 5). The average was calculated from array of measurement over a sheet (example show in table 1below)

TABLE 1 resistance measurements across a sheet.

| Batch Number | T0004 | | | Multimeter | CAL0062 | |
|---|---|---|---|---|---|---|
| Sheet | 2 | | | | | |
| Row | Column 2 | Column 5 | Column 8 | Column 11 | Column 14 | Column 17 |
| A | 1351 | 1350 | 1364 | 1336 | 1326 | 1368 |
| C | 1362 | 1378 | 1371 | 1340 | 1362 | 1385 |
| E | 1376 | 1405 | 1392 | 1399 | 1405 | 1411 |
| G | 1423 | 1446 | 1439 | 1444 | 1448 | 1498 |

EXAMPLE 3

In order to investigate the relationship between the thickness of the Carbon layer and the resistance of the carbon layer, some PET sheets were printed with different carbon thicknesses. To do so, the carbon printing and drying stages were repeated up to four times. The printed cards thus had 1, 2, 3or 4layers of carbon, giving carbon heights of between 17-56μm.

The thickness profiles of the printed tracks and pads were 20measured using a Mitutoyo Surftest SV-2000talystep.

The resistance of the spare carbon leg was calculated by measuring the short circuit current using an Autolab PGSTAT12potentiostat.
Methods Testing Protocol: Ru hexaammine solution was deposited in the well and a cyclic voltamcgram recorded at 100mVs$^{-1}$.

Ru Hexaaimnine Test Solution: The Ru hexaammine test solution consisted of 10mM [Ru(NH$_3$)$_6$)]Cl$_3$(Alfa Aesar, 010511) in Tris pH 9buffer (Sigma, T-1444) with 100mM KCl BDH, 101984L), 50mM MgSO$_4$(Sigma, M-5921) and 1% Sodium Taurocholate (Sigma T40095G).

At the end of the Standard printing process, the cards were cut to form wells and the thickness profiles of the carbon spare legs were measured. The design was as shown in FIG. 3a. Stripe with different carbon thicknesses were then ruthenium tested according to the protocol described above.

Figure 6:
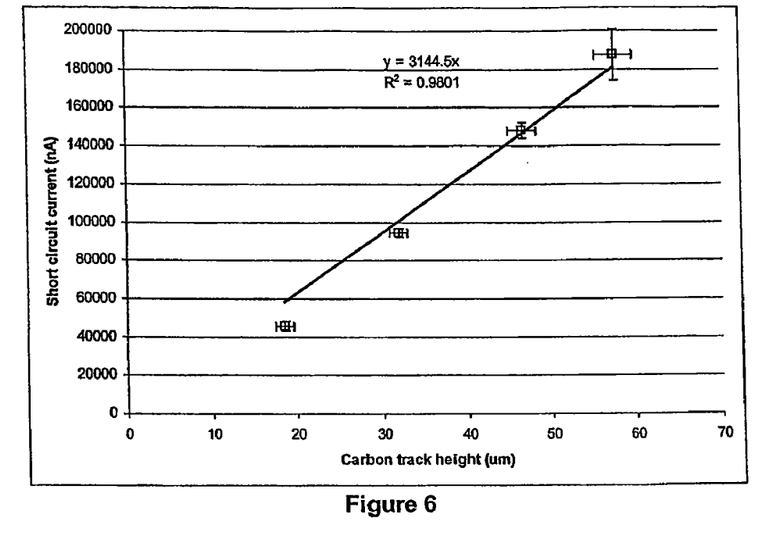
FIG. 6 is a graph showing correlation of short circuit current with carbon track height thickness.

The graph in FIG. 6 presents the variation of the short circuit current as a function of the carbon track height. The short circuit measurement is linearly linked to the track and thus to the electrode thickness.

Figure 7:
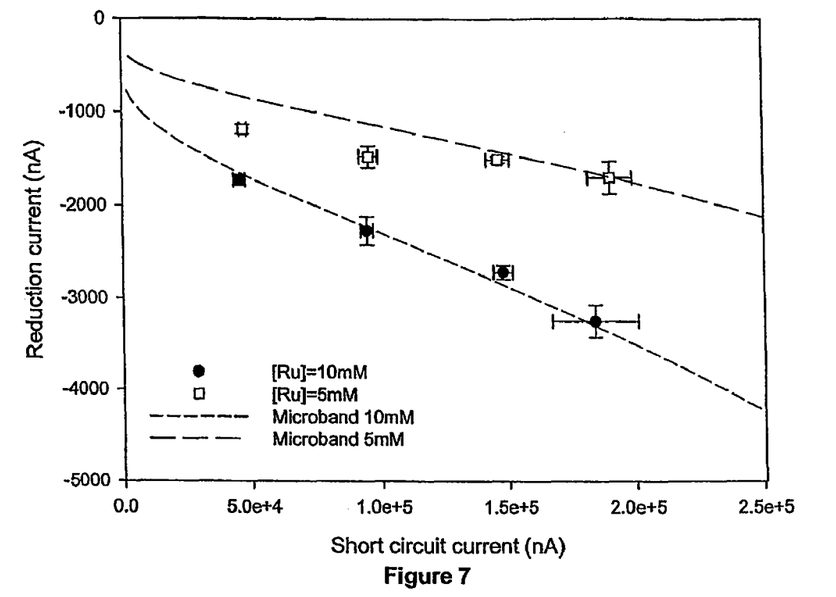
FIG. 7 is a graph showing reduction current, versus short circuit currents for two ruthenium (Ru) Concentrations (5mM and 10mM)

Since it is known how the short circuit current is related to. the electrode thickness, it is then possible to plot the reduction current versus the short circuit current (FIG. 7) for two ruthenium concentrations: 5and 10mM. The reduction current grows with the short circuit current increase in agreement with the microband equation:

$$i(t) = \frac{2\pi w FADC}{w \ln\left(64 \frac{Dt}{w^2}\right)}$$

Where
w is the width of the band electrode (cm)
A=2πrw where r (cm) is the radius of the microband
F is the Faraday constant (96485C.mol$^{-1}$)
D is the diffusion coefficient for Ru(4.8×10$^{-6}$cm$^2$.s$^{-1}$determined from previous experiments)
C is the concentration of Ru (mol.cm$^{-3}$)
This response augmentation obeys to the microband behaviour over the whole panel of investigated thicknesses.

It is also observed that over the range of studied thicknesses, the variation of the reduction current as a function of the short circuit is close to linearity. A simple linear fit can then be used to compensate for the variation in the electrode thickness.
[Ru]=10mM: y=−0.0105x−1242.4($R^2$=0.9927)
[Ru]=5mM: y=−0.0033x−1069.3($R^2$=0.9102)
Where y is the reduction current (nA)
And x is the short circuit current (nA)

Figure 8:
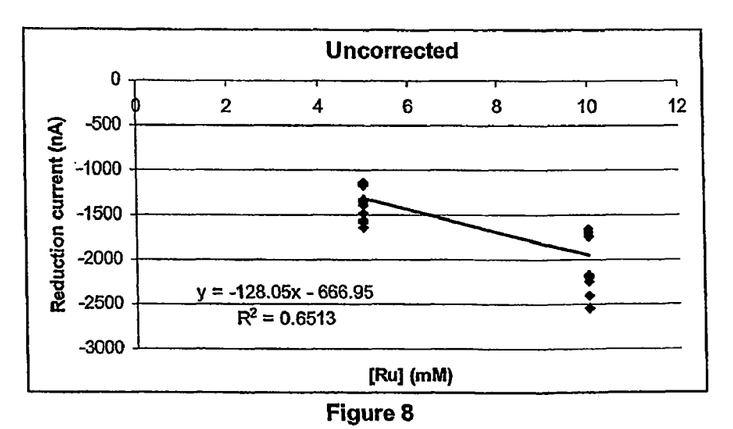
FIG. 8 is a plot showing reduction current versus Ru concentration before applying the correction factor.

The composite calibration obtained by plotting together the results from the 17μm and 31μm carbon thicknesses is shown in FIG. 8.

TABLE 2a

Coefficient of variation before the correction factor was applied.

| Concentration [Ru] (mM) | Average reduction current (nA) | CV (%) |
|---|---|---|
| 5 | −1307.19 | 12.91 |
| 10 | −1973.81 | 14.86 |

Figure 9:
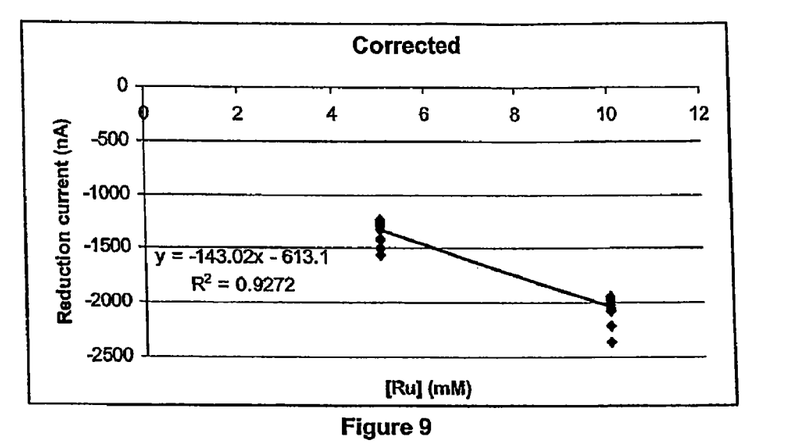
FIG. 9 is a plot, similar to that of FIG. 8, but showing reduction current versus Ru concentration after applying the correction factor.

It is then possible to correct the reduction current values by using the short circuit measurements and the previous equations. All the reduction current values were corrected to a same short circuit value of 75000nA which is the median value. The corrected calibration is plotted in FIG. 9.

TABLE 2b

Coefficient of variation after the correction factor was applied.

| Concentration [Ru] (mM) | Average reduction current (nA) | CV (%) |
|---|---|---|
| 5 | −1328.19 | 7.77 |
| 10 | −2043.27 | 5.05 |

The electrode thickness compensation allows the global coefficient of variation (CV) to be reduced from 13.89% to 6.4%. The reproducibility is therefore improved thanks to the correction.

Between the first sheets printed at the beginning of a batch and the ones produced at the end, the short circuit current values vary from 47300to 51200nA. It corresponds to a variation from 15.0μm to 16.3μm in carbon thickness.

These results show that it is possible to compensate the variation in electrochemical response due to the electrode thickness variability by measuring the short circuit current. This later is linked to the electrode thickness and can be used to correct the measured current.

EXAMPLE 4

Resistance Compensation Implemented Via a Data Tag Barcode

The barcode may consist of encoded non-variable and variable data associated with a product, for example:

| Product Code (PPP) | Expiry | | |
|---|---|---|---|
| Date (DDMMMYY) | Lot/Batch Number (BATCH) | Calibration | |
| Data (CALIBRATION) | | | |

Initially this barcode will be the same for each strip within a batch. The compensation resistance value for the batch will be calculated (for example using the methods shown in example 3) and will be included within the calibration information for the barcode. For example: if a value of 1.975kOhms is calculated, then the 1975will be included within the calibration information. This will then be read by an associated electronic device to perform a correction or be looked up against a known curve/equation.

The batch compensation resistance value will be measured from the additional leg electrode or test-points and calculated prior to printing the product barcode during the manufacturing process.

So the barcode for this batch could be: PPP DDMD4IYY BATCH CALIBRA1975

Equally each strip could have it own strip barcode with the individual compensation resistance or value. For example 5strips in a Batch with Batch Number 12345could have the following compensation values:

| Strip | Compensation Value | Strip Barcode |
|---|---|---|
| 1 | 1.975 | PPP DDMMMYY 12345 CALIBRA1975 |
| 2 | 1.982 | PPP DDMMMYY 12345 CALIBRA1982 |
| 3 | 1.756 | PPP DDMMMYY 12345 CALIBRA1756 |
| 4 | 1.888 | PPP DDMMMYY 12345 CALIBRA1888 |
| 5 | 1.903 | PPP DDMMMYY 12345 CALIBRA1903 |

Again, these compensation values will be used by the electronic device to correct via a look up table, curve or equation. The manufacturing process may be set up to measure the compensation from an additional strip leg during packaging and print the strip barcode as the individual strip is packed.

It will be appreciated that any of the cell designs described in WO 03/056319may be used in conjunction with the invention.

Having thus described the present invention by reference to a preferred embodiment it is to be well understood that the embodiment in question is exemplary only and that modifications and variations such as will occur to those possessed of appropriate knowledge and skills may be made without departure from the spirit and scope of the invention as set forth in the appended claims and equivalents thereof. In the claims, any reference. signs placed in parentheses shall not be construed as limiting the claims. The word "comprising" and "comprises," and the like, does not exclude the presence of elements or steps other than those listed in any claim or the specification as a whole. The singular reference of an element does not exclude the plural reference of such elements.

We claim:

1. A method for determining a scaling factor for scaling an output of a sensor comprising a first electrochemical cell having at least one working electrode, to compensate for the effect on the output caused by any variation in a value of a physical dimension of the working electrode from a reference value of the physical dimension, the method comprising:
   obtaining a first measured value from a portion of material being at least one conductive track formed on the sensor so as to have the same value of the physical dimension as does the working electrode;
   determining a second value that relates to the reference value of the physical dimension; and
   generating a scaling factor from the first measured value and the second value that relates to the reference value of the physical dimension.

2. A method according to claim 1 wherein the physical dimension is thickness or width.

3. A method according to claim 1, wherein the first measured value is dependent upon the electrical resistance of the portion of material, which portion is formed from the same material as and has the same thickness as the working electrode of the first cell.

4. A method according to claim 3, wherein the portion of material and the first cell are formed on a common substrate and the first measured value is a current value obtained when a predetermined voltage is applied between the portion of material and the at least one conductive track also formed on the substrate.

5. A method according to claim 4 wherein the track electrically connects to a pseudo-reference electrode of the first cell.

6. A method according to claim 1 wherein the second value is a measured value that relates to the average thickness of the working electrodes of a batch of cells.

7. A method according to claim 6 wherein, the second measured value is dependent upon the average electrical resistance of a plurality of tracks, each track of the plurality of tracks being formed on a separate common substrate with a respective one of the cells from the batch of cells and formed from the same material as and having the same thickness as the working electrode of the respective one of cells of the batch of cells.

8. A method according to claim 7, wherein the second measured value is obtained by, for each track of the plurality of tracks, applying a predetermined voltage between that track and a further track formed on a common substrate with that track to obtain a current value; and
   averaging the obtained current values to obtain the second measured value.

9. A method according to claim 8 wherein each of the plurality of further tracks electrically connects to a pseudo-reference electrode of a respective cell of the plurality of cells.

10. A method according to claim 1 wherein the second value relates to a thickness of a national working electrode.

11. A method of scaling a measurement of an output of an electrochemical cell, the method comprising:
    taking a measurement of an output of the electrochemical cell;
    scaling the measurement using a scaling factor obtained by the method of any preceding claim.

12. A meter configured to perform the method of claim 11.

13. A sensor comprising at least one electrochemical cell having a working electrode and a counter electrode and a pair of tracks by means of which a voltage may be applied across the electrodes, the sensor further comprising a portion of material arranged for use as the portion of material in the method of claim 1.

* * * * *